(12) United States Patent
Buschke (10) Patent No.: US 7,314,444 B2
(45) Date of Patent: Jan. 1, 2008

(54) MEMORY ASSESSMENT BY RETRIEVAL SPEED AND USES THEREOF

(75) Inventor: Herman Buschke, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 352 days.

(21) Appl. No.: 10/350,155

(22) Filed: Jan. 23, 2003

(65) Prior Publication Data

US 2003/0181793 A1 Sep. 25, 2003

Related U.S. Application Data

(60) Provisional application No. 60/351,864, filed on Jan. 25, 2002.

(51) Int. Cl.
*A61B 5/00* (2006.01)
(52) U.S. Cl. .................. 600/300; 128/920; 434/236
(58) Field of Classification Search ........ 600/300–301, 600/559, 544–545; 434/236–238, 258–262, 434/365; 128/898, 920; 273/273, 459–460
See application file for complete search history.

(56) References Cited

U.S. PATENT DOCUMENTS

| | | |
|---|---|---|
| 4,770,636 A | 9/1988 | Buschke |
| 5,079,726 A | 1/1992 | Keller |
| 5,230,629 A | 7/1993 | Buschke |
| 5,411,271 A | 5/1995 | Mirando |
| 6,306,086 B1 | 10/2001 | Buschke |
| 6,964,638 B2 * | 11/2005 | Theodoracopulos et al. ............. 600/300 |

OTHER PUBLICATIONS

Kuslansky, G. et al., entitled "Screening for Alzheimer's disease; the memory impairment screen versus the conventional three-word memory test," J Am Geriatr Soc Jun. 2002; 50(6): 1086-91.
Buschke, H et al., entitled "Screening for dementia with memory impairment screen," Neurology Jan. 15, 1999; 52(2): 231-8.
Buschke, H et al., entitled "Diagnosis of early dementia by the Double Memory Test: encoding specificity improves diagnostic sensitivity and specificity," Neurology Apr. 1997; 48(4): 989-97.
Gardiner et al., entitled "How Level of Processing Really Influences Awareness in Recognition Memory," Can J Exp Psychol, 50: 114-122, 1996.
Tulving E, entitled "Memory and Consciousness," Can Psychol, 26: 1-12, 1985.

* cited by examiner

*Primary Examiner*—Max F. Hindenburg
*Assistant Examiner*—Michael C Astorino
(74) *Attorney, Agent, or Firm*—Amster, Rothstein and Ebenstein LLP (57) ABSTRACT

The present invention provides methods for assessing episodic memory in a subject. Also provided are methods for assessing semantic memory in a subject. The present invention further provides methods for screening for an agent directed to treating, slowing down the progress of, attenuating the symptoms of, or preventing dementia characterized by episodic memory impairment. Additionally, the present invention provides methods for screening for an agent directed to treating, slowing down the progress of, attenuating the symptoms of, or preventing dementia characterized by semantic memory impairment. Finally, the present invention provides methods for measuring semantic memory in a subject.

45 Claims, 1 Drawing Sheet

Figure 1

MEMORY ASSESSMENT BY RETRIEVAL SPEED AND USES THEREOF

CROSS REFERENCE TO RELATED APPLICATIONS

This application claims the benefit of U.S. Provisional Application No. 60/351,864, filed Jan. 25, 2002.

STATEMENT OF GOVERNMENT INTEREST

This invention was made with government support under NIA Grant No. AG03949. As such, the United States government has certain rights in this invention.

BACKGROUND OF THE INVENTION

It is estimated that, over the next twenty years, one in every five persons will be over the age of 65. With this new demographic profile will come an increase in a wide variety of age-related conditions, including Alzheimer's disease ("AD") and other forms of dementia. Dementia is a syndrome of progressive decline, in multiple domains of cognitive function, that eventually leads to an inability to maintain normal social and/or occupational performance. At present, AD is the most common type of dementia, afflicting approximately 4 million Americans. One in ten persons over the age of 65, and nearly half of those over the age of 85, suffer from AD, and AD is the fourth leading cause of death in the U.S. The cost to American society is estimated to be at least $100 billion every year, making AD the third most costly disorder of aging.

Early identification is critical in progressive conditions such as AD, because earlier treatment may be more effective than later treatment in preserving cognitive function. Furthermore, early detection may allow time to explore options for treatment and care. Nevertheless, early detection is compromised by the failure of many patients to report to their treating physicians such early symptoms of AD as memory lapses and mild, but progressive, deterioration of specific cognitive functions, e.g., language (aphasia), motor skills (apraxia), and perception (agnosia). In addition, studies have documented the difficulty experienced by even well-trained health care professionals in correctly diagnosing AD and other forms of dementia (1). Accordingly, a simple, sensitive, reliable, and easily-administered AD diagnostic test would be of great assistance in targeting individuals for early intervention.

The earliest manifestation of AD is often memory impairment—a requirement in each of the two sets of criteria for diagnosis of dementia that are commonly used: the National Institute of Neurological and Communicative Disorders and Stroke/Alzheimer's Disease and Related Disorders Association (NINCDS/ADRDA) criteria, which are specific for Alzheimer's disease, and the American Psychiatric Association's Diagnostic and Statistical Manual of Mental Disorders, $4^{th}$ ed. (DSM-IV) criteria, which are applicable for all forms of dementia. Therefore, any test for AD or dementia that is associated with memory impairment should be most sensitive for the early detection of memory impairment.

Conventional memory tests are not optimal for the detection of mild dementia or the early stages of Alzheimer's disease. Some of these tests are inappropriately sensitive to the patient's educational level (2). They also may fail to test for certain types of memory loss that are typical of early dementia or AD. In addition, they may fail to reflect whether compounds or therapies that are administered to treat dementia have the desired effects. Furthermore, these tests frequently suffer from a high rate of false positives (low specificity).

Essentially all tests of memory, including tests of learning, retention, recall and/or recognition (hereinafter referred to as "memory tests"), involve serial-processing memory. "Serial-processing memory" acknowledges the limitations in a subject's input and output processing, which limitations permit the subject to process only one item at a time during input (receiving information) and output (recalling or retrieving information). In this sense, "memory" comprises units of received information and recalled information. In most tests of serial-processing memory, multiple items are presented serially to a subject, one item at a time, until all of the items have been presented ("serial presentation"), and the subject reports the remembered items serially, one item after another, in the order in which they were originally presented ("serial recall"). Items may be presented verbally, visually, or by any other suitable means.

Although there are many variations, a typical memory test consists of two main steps. First, the tester presents to the subject a number of items (e.g., bowl, zebra, orange, anger) to be recalled from memory. The items may be presented orally, in writing, in pictures, or by any other suitable means. Sometimes, the subject is also supplied with a cue associated with each or some of the items on the list. Typically, the cue is the category that encompasses the associated item, or that defines an aspect of the associated item. For example, the cue "animal" or "stripes" might be presented in association with the item "zebra". Certain conventional, paired-associates tests use unrelated nouns as cues for test items.

The presentation of items in association with cues, wherein the subject first must identify an item from its cue, is known as "controlled learning". Controlled learning is used in memory tests to ensure the attention of the subject and the equal processing of all of the items in a list. In addition, controlled learning demonstrates that the subject can identify items from their cues. Controlled learning also induces encoding specificity, by providing cues at the time of encoding information that later can be used to aid recall. The correct identification of items, by matching the items with their associated cues, verifies that the required processing was performed by the subject. Controlled learning may be performed by normal individuals, and by those with dementia or others type of cognitive decline.

In the next step, the subject is asked to recall the items presented to her in the list, either from memory, without presentation of the associated cue, in any order (free recall), or following presentation of the associated cue (cued recall). Cued recall may be used selectively to facilitate recall of those items not first recalled by free recall (recall in any order, without presentation of any cues).

One variation of the standard memory test involves an additional step for "controlled rehearsal", wherein the subject is instructed to repeat each item as it is presented. Alternately, the subject may be asked to repeat the preceding item as the current item is presented, or the subject may be instructed to repeat both the preceding item and the current item. As with controlled learning, controlled rehearsal ensures the attention of the subject and the equal processing of all items, and demonstrates that the required processing was performed by the subject.

Some memory tests, particularly tests of delayed recall or forgetfulness, utilize interference delays between memory trials. Interference delays are periods of time between memory trials, wherein an unrelated task (e.g., counting, spelling) is performed by the subject to prevent rehearsal. As another alternative, the tester may maintain a constant number of items to be learned by the subject. This step, referred to as "contingent learning", can be accomplished by adding new items to the list as the old items are learned.

"Controlled reminding" refers to an additional step wherein the subject is reminded of items that were not recalled during each trial. In free-recall memory tests, the subject is not reminded of the items that were not recalled until after he has been given the opportunity to recall as many items as possible. In the case of cued recall, the subject is reminded of the item before the next cue is presented. Controlled reminding may be either "selective reminding", wherein the subject is reminded each time the item is not recalled, or "restricted reminding", wherein the subject is reminded only until the item is recalled once, either with or without presentation of the item.

Memory tests known in the art include various combinations of the foregoing elements and steps. For example, the memory component of the Free and Cued Selective Recall Test ("FCRST") comprises an initial controlled-learning step, wherein the patient first must identify items from their associated cues. The patient then must recall as many of the test items as possible (typically sixteen) from their associated category cues. Following a brief interference delay, the patient is then asked to recall as many of the presented items as she can by free recall (i.e., recall in any order, without the associated cues), followed by cued recall for items not remembered by free recall. If there are multiple trials, the subject is then selectively reminded of missed items (i.e., reminded each time an item is not recalled) before the next recall trial. The score for total recall is the total of uncued responses and cued responses, with each response (whether cued or uncued) worth one point.

Conventional memory tests are scored by tallying the total number of items recalled from a list of items previously presented to the subject, either within any one testing trial or across many testing trials. Each item recalled is accorded the same weight—a method known as "unit counting" or "unweighted counting"—so that a subject recalling items 1 to 5 of a ten-item list would be judged to have the same measure of memory as a subject who recalled items 6 to 10 of the same ten item list. Furthermore, a subject recalling items 1 to 5 of a ten-item list in a first trial, and items 6 to 10 of the list in a second trial, would be considered to have the same measure of memory as a subject who recalled items 1 to 5 in the first and second trials, but could not recall items 6 to 10 at all. Memory tests utilizing this type of unweighted counting assume that all of the items presented and retrieved are equal in value, i.e., that the probability of encoding, learning, and retaining any single item is equal to the probability of encoding, learning, and retaining any other items.

However, items in a presented list differ in likelihood of recall, depending upon a number of factors. Serial processing at input and output often results in "serial-position effects", which are differences in the frequency of recall among list items due to the order in which the items are presented. In this regard, some items are "easier" or "more difficult" to recall, depending upon the order in which such items are presented to the subject. These serial-position effects are illustrated for test groups in serial-position curves, which are graphs that show the percentage of subjects recalling the items of a list versus the order in which the items are presented or recalled.

Serial-position effects demonstrate that the probability of recall may be affected by the order in which test items are presented ("presentation order"), or the order in which test items are recalled ("recall order"), or both. Important serial-position effects include "primacy", in which there is a higher recall of earlier presented items, and "recency", in which there is a higher recall of the items most recently presented. An analysis of serial-position effects is important because the manifestation of certain serial-position effects (or the lack thereof) may be associated with dementia. For instance, recall by normal aged subjects is characterized by both primacy and recency effects, whereas recall by aged subjects with AD is characterized only by recency effects.

Additionally, unweighted counting disregards qualitative differences in memory impairment, e.g., where impairment in total memory is a result of deficiencies in a particular stage or facet of the memory process, such as a deficiency in encoding information, learning information, or retaining information. Such qualitative differences may be essential for the diagnosis of AD or dementia characterized by memory impairment, and may be instrumental in ensuring the appropriate targeting of, and evaluation of the efficacy of, therapeutics directed to the treatment of AD or early dementia.

In view of the foregoing, the measurement of memory by unweighted counting (unit weighting) may not be justified. Although unweighted counting provides a lower bound for memory performance, it sacrifices statistical power by disregarding essential information about the serial-position characteristics of retrieved items (including probability of retrieval), and about the various processes involved in memory (including encoding, learning, and retention). A method of measuring memory that preserves information about the serial-position effects of retrieved items, or that recognizes deficiencies in certain elements of total memory, would improve the assessment of memory performance, aid in the earlier diagnosis of AD and dementia, and permit the sophisticated screening of therapeutics directed to the treatment of AD and dementia.

SUMMARY OF THE INVENTION

All memory tests necessarily involve serial-processing memory, including, without limitation, tests of biographical or historical recall, tests of narrative recall, tests of auditory or visual input, and category-fluency tests of semantic memory. Therefore, the design and structure of memory tests and experiments are limited to serial-processing memory tests and experiments that test a subject's ability to encode, retain, and/or retrieve items, one at a time, as part of a serial collection of items. Furthermore, the encoding, retention, and/or retrieval of each item is conditioned by the serial encoding, retention, and retrieval of other items that precede and follow each item in presentation and recall.

However, not all items presented or retrieved by a subject are equal in value. Accordingly, the probability of encoding, learning, and retaining any single item is not necessarily equal to the probability of encoding, learning, and retaining any other item, and can depend upon a wide variety of parameters, including presentation order and speed of recall. Some items are "more difficult" to recall than others, as shown by slower retrieval speeds. Additionally, the frequencies and types of items not recalled by a subject can establish memory impairment, and may be indicative of AD or other dementias associated with memory impairment.

The inventor has demonstrated herein that the discrimination of Alzheimer's disease from other dementias involving memory impairment can be improved by measuring a subject's item-specific retrieval speeds, wherein more credit is given for faster recall and less credit is given for slower recall. Slower recall by individuals with memory impairment will reduce their memory scores, and faster recall by individuals without memory impairment will increase their memory scores, thereby increasing the difference (effect size) between the memory scores of those with memory impairment and those without memory impairment.

The present invention is directed to various methods of assessing and measuring episodic memory and semantic memory in a subject, comprising the use of item-specific retrieval speeds in the administration and analysis of all types of serial-processing memory tests. Since all items are not necessarily retrieved from memory with the same ease or speed, item-specific speed of recall may be assessed in order to amplify and/or recognize deficiencies in memory, i.e., deficiencies in recall, learning, and retention. Accordingly, the methods of the present invention improve the assessment of memory performance, and aid in the earlier diagnosis of dementia characterized by memory impairment, including, but not limited to, dementia associated with Alzheimer's disease.

It is understood that, in all of the methods of the present invention described herein, assigned values may be analyzed by calculating a score for the subject based on the retrieval speeds of recalled items, and then comparing the calculated score to a reference score. The reference score may establish memory impairment or may be indicative of a dementia characterized by memory impairment, including, but not limited to, dementia associated with Alzheimer's disease. Additionally, items may be weighted according to any convenient, useful, or desirable parameter, including, but not limited to, retention weighting (presentation weighting, recall weighting, and total-retention weighting), recall state, normative weighting, amplification weighting, retrieval weighting, retrieval-speed weighting, and weighting based upon serial-position effects. Furthermore, the memory-assessment methods of the present invention may be used in conjunction with any form of serial-processing memory test. Finally, item-specific retrieval speeds may be determined within one memory trial, or across two or more memory trials.

The present invention first provides a method for assessing episodic memory in a subject by presenting to a subject a list of items to be retrieved from episodic memory by the subject; having the subject retrieve the presented items from episodic memory; determining the subject's retrieval speed for each of the items retrieved from episodic memory by the subject; and analyzing the retrieval speeds for the retrieved items in order to assess episodic memory and determine memory impairment.

The present invention further provides a method for assessing episodic memory in a subject by presenting to a subject a list of items to be retrieved from episodic memory by the subject; having the subject retrieve the presented items from episodic memory; determining the subject's retrieval speed for each of the items retrieved from episodic memory by the subject; assigning a separate weighted value to each of the retrieved items, wherein the value for each retrieved item is weighted according to the speed with which the item is retrieved by the subject; and analyzing the assigned values of the retrieved items in order to assess episodic memory and determine memory impairment.

Additionally, the present invention provides a method for screening for an agent directed to treating, slowing down the progress of, attenuating the symptoms of, or preventing dementia characterized by episodic memory impairment by: (a) assessing episodic memory by one of the methods disclosed herein, so as to obtain a first score; (b) providing a candidate agent to a subject; (c) performing the selected method of step (a) on the subject to obtain a second score; and (d) analyzing the effect of the candidate agent on the second score by comparing the first score to the second score.

Also provided is a method for measuring episodic memory in a subject by presenting to a subject a list of items to be retrieved from episodic memory by the subject; having the subject retrieve the presented items from episodic memory; determining the subject's retrieval speed for each of the items retrieved from episodic memory by the subject; and counting the number of retrieved items for which the retrieval speed is equal to, or less than, a reference speed.

Additionally, the present invention provides a method for assessing semantic memory in a subject by presenting to a subject a cue for retrieving at least one item from semantic memory; having the subject retrieve at least one item from semantic memory; determining the subject's retrieval speed for each of the items retrieved from semantic memory by the subject; and analyzing the retrieval speeds for the retrieved items in order to assess semantic memory and determine memory impairment.

The present invention further provides a method for assessing semantic memory in a subject by presenting to a subject a cue for retrieving at least one item from semantic memory; having the subject retrieve at least one item from semantic memory; determining the subject's retrieval speed for each of the items retrieved from semantic memory by the subject; assigning a separate weighted value to each of the retrieved items, wherein the value for each retrieved item is weighted according to the speed with which the item is retrieved by the subject; and analyzing the assigned values of the retrieved items in order to assess semantic memory and determine memory impairment.

The present invention further provides a method for screening for an agent directed to treating, slowing down the progress of, attenuating the symptoms of, or preventing dementia characterized by semantic memory impairment by: (a) assessing semantic memory by one of the methods disclosed herein, so as to obtain a first score; (b) providing a candidate agent to a subject; (c) performing the selected method of step (a) on the subject to obtain a second score; and (d) analyzing the effect of the candidate agent on the second score by comparing the first score to the second score.

Finally, the present invention provides a method for measuring semantic memory in a subject by presenting to a subject a cue for retrieving at least one item from semantic memory; having the subject retrieve at least one item from semantic memory; determining the subject's retrieval speed for each of the items retrieved from semantic memory by the subject; and counting the number of retrieved items for which the retrieval speed is equal to, or less than, a reference speed.

Additional objects and embodiments of the present invention will be apparent in view of the description which follows.

DETAILED DESCRIPTION OF THE INVENTION

The present invention provides a method for assessing episodic memory in a subject. The subject is preferably a mammal (e.g., an ape, a human, a lemur, a monkey, and other primates), and is most preferably a human. As used herein, "episodic memory" refers to a cognitive model of normal recognition proposed by Tulving (7), wherein recollection-based recognition, or "remembering," is accompanied by contextual information about the episode in which an item was encountered. The method of the present invention comprises the following: presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; and analyzing the retrieval speeds for the retrieved items in order to assess episodic memory and determine memory impairment. Memory involves three main processes: encoding, retention, and retrieval. As used herein, the term "retrieval speed" refers to the time that is required for a subject to recall or retrieve an item from memory.

In the method of the present invention, a subject's retrieval speed may be determined by a number of different methods. For example, a subject's retrieval speed may be determined by measuring the subject's item-specific speed of cued recall. "Cued recall" is tested when a subject is asked to recall from memory an item presented to him/her in a list, following presentation of a cue previously associated with that item. Cued recall may be used selectively to facilitate recall of those items not first recalled by free recall (recall in any order, without presentation of any cues). One example of cued recall for use in the method of the present invention is cued recall after controlled learning. Controlled learning, in this context, may be used, in part, to elicit from a subject as many items as possible, in order to obtain as many speed measurements as possible. Additionally, controlled learning may be used in this context to assist a subject in operating at his/her optimum speed. Controlled learning is particularly useful in the method of the present invention because most individuals, including normal individuals and those with dementia or others type of cognitive decline, are capable of controlled learning.

In accordance with the method of the present invention, other examples of methods for determining a subject's retrieval speed include, without limitation, measuring the subject's item-specific speed of paired-associates learning; measuring the subject's item-specific speed of free recall; and measuring the subject's item-specific speed of serial recall. "Free recall" is tested when a subject is asked to recall from memory, in any order, each item presented to him/her in a list, without presentation of an associated cue or other means of assisting in recall. In most tests of serial-processing memory, multiple items are presented serially to a subject, one item at a time, until all of the items have been presented ("serial presentation"); the subject reports the remembered items serially, one item after another, in the order in which they were originally presented ("serial recall"). Items may be presented verbally, visually, or by any other suitable means.

In accordance with the method of the present invention, various methods may be used to measure item-specific retrieval speed, including digital timepieces (e.g., a clock or stop-watch), analogue timepieces (e.g., a clock or stop-watch), and computerized timepieces. Additionally, various methods may be used to analyze the retrieval speed for each of the items retrieved from episodic memory by a subject. For example, one such method comprises calculating an episodic memory score for a subject based on the retrieval speeds, and comparing the episodic memory score to a reference score. In one embodiment of the present invention, the reference score establishes episodic memory impairment in relation to a chosen reference group or in relation to an earlier score obtained by the subject. This episodic memory impairment may be indicative of various states of cognitive decline, including, without limitation, pre-clinical Alzheimer's disease, early Alzheimer's disease, mild cognitive impairment (MCI), age-related cognitive decline, mild neurocognitive disorder, delirium, and dementia.

As used herein, the term "MCI" refers to a condition of mild memory impairment that may be found in high-risk individuals with low recall. "MCI" is defined in the art to mean that a subject's recall is 1.5 standard deviations below the norm for persons of his/her age group. Approximately 15% of all MCI subjects will develop dementia each year. Additionally, as used herein, the term "age-related cognitive decline" has been defined by the DSM-IV to mean that a subject's recall is 1.0 standard deviations below the norm for persons of his/her age group.

The term "delirium", as used herein, refers to a clinical state that is characterized by fluctuating disturbances in arousal, attention, cognition, mood, and self-awareness. Delirium generally arises acutely; it may arise without prior intellectual impairment, or it may be associated with chronic intellectual impairment (3). There are many known causes of delirium, including infectious causes (e.g., acute meningitis, acute encephalitis, and infections outside of the brain), metabolic/toxic causes (e.g., anoxia, hypoglycemia, hypothyroidism, transient ischemia, and use of anticholinergic and other drugs), and structural causes (e.g., brain tumor, cerebral hemorrhage, cerebral infarction, and vascular occlusion) (3).

Additionally, as used herein, "dementia" refers to a chronic deterioration of cognitive skills, including intellectual function, that is severe enough to interfere with a person's ability to perform tasks and activities associated with daily living. There are many known causes of dementia, including infectious causes (e.g., bacterial endocarditis, Creutzfeldt-Jakob disease, tuberculous and fungal meningitis, and viral encephalitis), metabolic/toxic causes (e.g., anoxia, chronic drug/alcohol/nutritional abuse, hypoglycemia, hypothyroidism, and pellagra), and structural causes (e.g., Alzheimer's disease, brain tumor, cerebellar degeneration, head trauma, Huntington's chorea, Parkinson's disease, Pick's disease, and Wilson's disease) (3). In one embodiment of the present invention, the dementia is associated with Alzheimer's disease.

It is generally accepted that repeated activities become automatic, possibly because repeated information is taken out of random access memory (RAM), where it normally resides, and is made more easily retrievable. Accordingly, it is within the confines of the present invention to provide a method for assessing episodic memory in a subject, comprising multiple episodic-memory trials that use measurements of retrieval speed. For example, the above-described method may be repeated in one or more additional runs, so as to elicit from a subject the maximum number of items that s/he can recall, or so as to assess the rate at which a subject's retrieval speed increases across the trials.

In one embodiment of the present invention, the method of assessing episodic memory in a subject comprises the following: presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; performing at least one more memory trial (although as many trials may be employed as are deemed necessary by the skilled practitioner); and analyzing the retrieval speeds for the retrieved items, across the trials, in order to assess episodic memory and determine memory impairment.

In another embodiment of the present invention, the method of assessing episodic memory in a subject comprises the following: in a first trial, presenting to a subject a list of items to be retrieved from episodic memory by the subject, and determining (and, optionally, recording) the subject's retrieval speed for each of the items retrieved from episodic memory by the subject. Then, in a second trial, items not retrieved from episodic memory by the subject in the first trial are presented again, and the subject's retrieval speed for each of the items retrieved from episodic memory by the subject is determined (and, optionally, recorded). More trials may be performed, with or without "selective reminding" (reminding the subject, or repeating presentation of an item, each time an item is not recalled) or "restricted reminding" (reminding the subject, or repeating presentation of an item, each time an item is not recalled, but only until initial recall of the item). After the last trial, the retrieval speeds for the retrieved items, across the trials, may be analyzed in order to assess episodic memory and determine memory impairment.

The present invention further provides a method for assessing episodic memory in a subject using weighting of item-specific retrieval speeds. As used herein, "weighting" refers to the assignment of a numerical value to each item of a serial-processing memory test to be retrieved by a subject, wherein the value assigned to each item is determined according to phenomena observed upon the retrieval of each item. For example, in the method of the present invention, items may be weighted according to their retrieval speeds.

The method of the present invention comprises the following: presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; assigning (and, optionally, recording) a separate weighted value to each of the retrieved items, wherein the value for each retrieved item is weighted according to the speed with which the item is retrieved by the subject ("retrieval-speed weighting"); and analyzing the assigned values of the retrieved items in order to assess episodic memory and determine memory impairment. The subject is preferably a mammal (e.g., an ape, a human, a lemur, a monkey, and other primates), and is most preferably a human.

In the method of the present invention, a subject's retrieval speed may be determined by a number of different methods. For example, a subject's retrieval speed may be determined by measuring the subject's item-specific speed of cued recall. One example of cued recall for use in the method of the present invention is cued recall after controlled learning. Other examples of methods for determining a subject's retrieval speed include, without limitation, measuring the subject's item-specific speed of paired-associates learning and measuring the subject's item-specific speed of free recall.

In accordance with the method of the present invention, various methods may be used to measure item-specific retrieval speed, including digital timepieces (e.g., a clock or stop-watch), analogue timepieces (e.g., a clock or stop-watch), and computerized timepieces. Additionally, various methods may be used to analyze the retrieval speed for each of the items retrieved from episodic memory by a subject. For example, one such method comprises calculating an episodic memory score for a subject based on the retrieval speeds, and comparing the episodic memory score to a reference score. In one embodiment of the present invention, the reference score establishes episodic memory impairment in relation to a chosen reference group or in relation to an earlier score obtained by the subject. This episodic memory impairment may be indicative of various states of cognitive decline, including, without limitation, delirium, dementia (e.g., dementia associated with Alzheimer's disease), pre-clinical Alzheimer's disease, early Alzheimer's disease, mild cognitive impairment (MCI), age-related cognitive decline, and mild neurocognitive disorder. In one embodiment of the present invention, the dementia is associated with Alzheimer's disease.

In one embodiment of the present invention, the method for assessing episodic memory in a subject further comprises the introduction of a delay (e.g., an interference delay, delayed recall) between the steps of presenting to the subject the list of items and having the subject retrieve the presented items. For example, where an interference delay is introduced, a subject may be presented with a series of item, and may then be exposed to interference over the course of a short delay (e.g., 20 sec). Thereafter, the subject may be tested to see what s/he retained during the interference delay. An interference delay is useful in that it prevents rehearsing. With delayed recall, a subject may be required to wait a longer period of time (e.g., 30 min) before being asked to recall the items which had been presented. In such a case, recalled items are no longer in short-term memory.

In another embodiment of the present invention, the separated weighted values that are assigned to the retrieved items are further weighted by at least one other criterion. Examples of criteria for assigning weighted values in memory tests, and methods for testing memory using item-specific weighted memory measurements, are provided in U.S. Pat. No. 6,306,086, the contents of which are incorporated herein by reference in their entirety.

For example, items may be further weighted according to the difficulty of recall, so that items that are harder to recall (e.g., items that are recalled in any order, in the absence of any cues or other means to assist in recall, or "free recall") will be weighted more than items that are easier to recall (e.g., items that are recalled in response to a cue previously associated with that item, or "cued recall"). Additionally, items may be further weighted according to the length of retention by the subject before recall ("retention weighting"), e.g., by their order of presentation to the subject ("presentation weighting"), by their order of recall by the subject ("recall weighting"), or by the total period between presentation of the item and recall of the item by the subject ("total-retention weighting"). Furthermore, items may be weighted with respect to a group of normal subjects: items that are most often recalled by normal subjects (i.e., items that are easier to recall) are given less weight ("normative weighting"), and items that are less often recalled by normal subjects (i.e., items that are more difficult to recall) are given more weight. Items also may be weighted to enhance the differences between two groups, so that items typically recalled by one group, but not by another, are given greater weight ("amplification weighting"). Finally, each item may be weighted according to the speed with which it is recalled by members of a reference group.

Additionally, it is within the confines of the present invention to provide a method for assessing episodic memory in a subject, comprising multiple episodic-memory trials that use measurements of retrieval speed. For example, the above-described method may be repeated in one or more additional runs (although as many trials may be employed as are deemed necessary by the skilled practitioner), so as to elicit from a subject the maximum number of items that s/he can recall, or so as to assess the rate at which a subject's retrieval speed increases across the trials.

In one embodiment of the present invention, the method of assessing episodic memory in a subject comprises the following: presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; assigning (and, optionally, recording) a separate weighted value to each of the retrieved items, wherein the value for each retrieved item is weighted according to the speed with which the item is retrieved by the subject ("retrieval-speed weighting"); performing at least one more memory trials (although as many trials may be employed as are deemed necessary by the skilled practitioner); and analyzing the assigned values of the retrieved items, across the trials, in order to assess episodic memory and determine memory impairment. Although any additional type of weighting may be used, the assigned value of each item recalled in each trial is preferably weighted further according to whether the item had been recalled in the preceding and/or subsequent trial, i.e., each item is weighted according to its "recall state".

In another embodiment of the present invention, the method of assessing episodic memory in a subject comprises the following: in a first trial, presenting to a subject a list of items to be retrieved from episodic memory by the subject, determining (and, optionally, recording) the subject's retrieval speed for each of the items retrieved from episodic memory by the subject, and assigning (and, optionally, recording) a separate weighted value to each of the retrieved items, wherein the value for each retrieved item is weighted according to the speed with which the item is retrieved by the subject ("retrieval-speed weighting"). Then, in a second trial, items not retrieved from episodic memory by the subject in the first trial are presented again, and the subject's retrieval speed for each of the items retrieved from episodic memory by the subject is determined (and, optionally, recorded), and a separate weighted value is assigned to each of the retrieved items (and, optionally, recorded), wherein the value for each retrieved item is weighted according to the speed with which the item is retrieved by the subject ("retrieval-speed weighting"). More trials may be performed, with or without "selective reminding" (reminding the subject, or repeating presentation of an item, each time an item is not recalled) or "restricted reminding" (reminding the subject, or repeating presentation of an item, each time an item is not recalled, but only until initial recall of the item). After the last trial, the assigned values for the retrieved items, across the trials, may be analyzed in order to assess episodic memory and determine memory impairment. In a preferred embodiment of the present invention, each item is further weighted according to whether the item has been recalled in the preceding trial or the following trial and/or according to whether the item was recalled by the subject with or without reminding.

The present invention further provides a method for screening for an agent directed to treating, slowing down the progress of, attenuating the symptoms of, or preventing dementia characterized by episodic memory impairment. The dementia may be any of those disclosed herein, including dementia associated with Alzheimer's disease. Additionally, unless otherwise indicated, an "agent", as used herein, shall include a protein, polypeptide, peptide, nucleic acid (including DNA or RNA), antibody, Fab fragment, $F(ab')_2$ fragment, molecule, compound, antibiotic, drug, and any combinations thereof. A Fab fragment is a univalent antigen-binding fragment of an antibody, which is produced by papain digestion. A $F(ab')_2$ fragment is a divalent antigen-binding fragment of an antibody, which is produced by pepsin digestion. The antibody of the present invention may be polyclonal or monoclonal, and may be produced by techniques well known to those skilled in the art.

In accordance with the method of the present invention, a candidate agent is screened for efficacy in treating or preventing dementia characterized by memory impairment by comparing the performance of a subject or a group of subjects on any of the item-specific retrieval-speed memory tests of the present invention, prior to administration of the candidate agent, with the performance of the subject or the group of subjects on the same memory test, following administration of the candidate agent to the subject or the group of subjects. In the alternative, it is within the confines of the present invention to compare the results of item-specific retrieval-speed memory tests performed by control groups not receiving the candidate agent, with the results of item-specific retrieval-speed memory tests performed by test groups receiving the candidate agent.

By way of example, the method of the present invention may comprise the steps of: (a) assessing episodic memory by one of the methods disclosed herein, so as to obtain a first score; (b) providing a candidate agent to a subject; (c) performing the selected method of step (a) on the subject to obtain a second score; and (d) analyzing the effect of the candidate agent on the second score by comparing the first score to the second score. Episodic memory may be assessed, in order to obtain a first score, by presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; and analyzing the retrieval speeds for the retrieved items in order to assess episodic memory and determine memory impairment. Alternatively, episodic memory may be assessed, in order to obtain a first score, by presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; assigning (and, optionally, recording) a separate weighted value to each of the retrieved items, wherein the value for each retrieved item is weighted according to the speed with which the item is retrieved by the subject; and analyzing the assigned values of the retrieved items in order to assess episodic memory and determine memory impairment.

The methods described herein for assessing episodic and semantic memory using retrieval speeds, and for screening for an agent directed to treating, slowing down the progress of, attenuating the symptoms of, or preventing dementia characterized by memory impairment, may be useful for assessing any cognitive side-effects produced by pharmaceutical treatments or therapeutics (whether trial or otherwise). Additionally, these methods may be used to assess the effects of drugs directed to the treatment or prevention of Alzheimer's disease, other dementias characterized by memory impairment, and other conditions associated with cognitive decline.

The present invention also provides a method for measuring episodic memory in a subject. The subject is preferably a mammal (e.g., an ape, a human, a lemur, a monkey, and other primates), and is most preferably a human. The method of the present invention comprises the following: presenting to a subject a list of items to be retrieved from episodic memory by the subject; having the subject retrieve at least one of the presented items from episodic memory; determining (and, optionally, recording) the subject's retrieval speed for each of the items retrieved from episodic memory by the subject; and counting the number of retrieved items for which the retrieval speed is equal to, or less than, a reference speed. In one embodiment of the present invention, the reference speed is the speed at which occurs the greatest difference between the number of items retrieved by control subjects and the number of items retrieved by aged-with-dementia subjects. As disclosed herein, this reference speed may be determined by plotting a graph, for both control subjects and aged-with-dementia subjects, of the number of retrieved items versus time for retrieval, and then ascertaining the speed at which the number of items retrieved by the two populations differs to the greatest extent. Based upon data disclosed herein, an appropriate reference speed may be 1000 msec.

In the method of the present invention, a subject's retrieval speed may be determined by a number of different methods. For example, a subject's retrieval speed may be determined by measuring the subject's item-specific speed of cued recall. One example of cued recall for use in the method of the present invention is cued recall after controlled learning. Other examples of methods for determining a subject's retrieval speed include, without limitation, measuring the subject's item-specific speed of paired-associates learning and measuring the subject's item-specific speed of free recall.

The present further provides a method for assessing semantic memory in a subject. As used herein, "semantic memory" refers to a cognitive model of normal recognition, wherein familiarity-based recognition, or "knowing," is devoid of contextual information about the episode in which an item was encountered (8). The subject is preferably a mammal (e.g., an ape, a human, a lemur, a monkey, and other primates), and is most preferably a human. The method of the present invention comprises the following steps: presenting to a subject a cue for retrieving at least one item from semantic memory; having the subject retrieve at least one item from semantic memory; determining (and, optionally, recording) the subject's retrieval speed for each of the items retrieved from semantic memory by the subject; and analyzing the retrieval speeds for the retrieved items in order to assess semantic memory and determine memory impairment. In one embodiment of the present invention, the subject is primed before s/he is presented with a cue for retrieving at least one item from semantic memory.

In accordance with the method of the present invention, various methods may be used to determine a subject's retrieval speed for each of the items retrieved from semantic memory by the subject. For example, a fluency test may be administered to determine a subject's retrieval speed for each retrieved item. Examples of such fluency tests include, without limitation, measuring the subject's item-specific speed of antonym recall (one prompt per item) and measuring the subject's item-specific speed of retrieval in a category-fluency test (one prompt per class or category). Additionally, it is within the confines of the present invention to provide an additional step comprising priming the subject before s/he is asked to retrieve at least one item from semantic memory (i.e., before the second step).

In accordance with the method of the present invention, various methods may be used to measure item-specific retrieval speed, including digital timepieces (e.g., a clock or stop-watch), analogue timepieces (e.g., a clock or stop-watch), and computerized timepieces. Additionally, various methods may be used to analyze the retrieval speed for each of the items retrieved from semantic memory by a subject. For example, one such method comprises comparing the semantic memory score to a reference score. In one embodiment of the present invention, the reference score establishes semantic memory impairment in relation to a chosen reference group or in relation to an earlier score obtained by the subject. This semantic memory impairment may be indicative of various states of cognitive decline, including, without limitation, delirium, dementia (e.g., dementia associated with Alzheimer's disease), pre-clinical Alzheimer's disease, early Alzheimer's disease, mild cognitive impairment (MCI), age-related cognitive decline, and mild neurocognitive disorder. In one embodiment of the present invention, the dementia is associated with Alzheimer's disease.

Additionally, it is within the confines of the present invention to provide a method for assessing semantic memory in a subject, comprising multiple episodic-memory trials that use measurements of retrieval speed. For example, the above-described method may be repeated in one or more additional runs (although as many trials may be employed as are deemed necessary by the skilled practitioner), so as to elicit from a subject the maximum number of items that s/he can recall, or so as to assess the rate at which a subject's retrieval speed increases across the trials.

In one embodiment of the present invention, the method of assessing semantic memory in a subject comprises the following: presenting to a subject a cue for retrieving at least one item from semantic memory; having the subject retrieve at least one item from semantic memory; determining (and, optionally, recording) the subject's retrieval speed for each of the items retrieved from semantic memory by the subject; performing at least one more semantic-memory trial (although as many trials may be employed as are deemed necessary by the skilled practitioner); and analyzing the retrieval speeds for the retrieved items, across the trials, in order to assess semantic memory and determine memory impairment. It is also within the confines of the present invention to provide for a period of interference (e.g., an interference delay of 20 sec) between the first and second runs or trials to prevent the subject from refreshing his/her semantic memory.

Also provided by the present invention is a method for assessing semantic memory in a subject using weighting of item-specific retrieval speeds. The subject is preferably a mammal (e.g., an ape, a human, a lemur, a monkey, and other primates), and is most preferably a human. The method of the present invention comprises the following: presenting to a subject a cue for retrieving at least one item from semantic memory; having the subject retrieve at least one item from semantic memory; determining (and, optionally, recording) the subject's retrieval speed for each of the items retrieved from semantic memory by the subject; assigning (and, optionally, recording) a separate weighted value to each of the retrieved items, wherein the value for each retrieved item is weighted according to the speed with which the item is retrieved by the subject ("retrieval-speed weighting"); and analyzing the assigned values of the retrieved items in order to assess semantic memory and determine memory impairment.

In accordance with the method of the present invention, various methods may be used to determine a subject's retrieval speed for each of the items retrieved from semantic memory by the subject. For example, a fluency test may be administered to determine a subject's retrieval speed for each retrieved item. Examples of such fluency tests include, without limitation, measuring the subject's item-specific speed of antonym recall and measuring the subject's item-specific speed of retrieval in a category-fluency test.

In one embodiment of the present invention, the separate weighted values that are assigned to the retrieved items are further weighted by at least one other criterion. For example, items may be further weighted according to the difficulty of recall, so that items that are harder to recall (e.g., items that are recalled in any order, in the absence of any cues or other means to assist in recall, or "free recall") will be weighted more than items that are easier to recall (e.g., items that are recalled in response to a cue previously associated with that item, or "cued recall"). Additionally, items may be further weighted according to the length of retention by the subject before recall ("retention weighting"), e.g., by their order of presentation to the subject ("presentation weighting"), by their order of recall by the subject ("recall weighting"), or by the total period between presentation of the item and recall of the item by the subject ("total-retention weighting"). Furthermore, items may be weighted with respect to a group of normal subjects, so that items most often recalled by normal subjects are given more weight ("normative weighting"). Items also may be weighted to enhance the differences between two groups, so that items typically recalled by one group, but not by another, are given greater weight ("amplification weighting"). Finally, each item may be weighted according to the speed with which it is recalled by members of a reference group.

In accordance with the method of the present invention, various methods may be used to measure item-specific retrieval speed, including digital timepieces (e.g., a clock or stop-watch), analogue timepieces (e.g., a clock or stop-watch), and computerized timepieces. Additionally, various methods may be used to analyze the weighted values that are assigned to the items retrieved from semantic memory by a subject. For example, one such method comprises calculating a semantic memory score for the subject based on the weighted values, and comparing the semantic memory score to a reference score. In one embodiment of the present invention, the reference score establishes semantic memory impairment in relation to a chosen reference group or in relation to an earlier score obtained by the subject. This semantic memory impairment may be indicative of various states of cognitive decline, including, without limitation, delirium, dementia (e.g., dementia associated with Alzheimer's disease), pre-clinical Alzheimer's disease, early Alzheimer's disease, mild cognitive impairment (MCI), age-related cognitive decline, and mild neurocognitive disorder. In one embodiment of the present invention, the dementia is associated with Alzheimer's disease.

The present invention also provides a method for screening for an agent directed to treating, slowing down the progress of, attenuating the symptoms of, or preventing dementia characterized by semantic memory impairment. An "agent", as used herein, shall include a protein, polypeptide, peptide, nucleic acid (including DNA or RNA), antibody, Fab fragment, $F(ab')_2$ fragment, molecule, compound, antibiotic, drug, and any combinations thereof, as defined above. The subject is preferably a mammal (e.g., an ape, a human, a lemur, a monkey, and other primates), and is most preferably a human.

In accordance with the method of the present invention, a candidate agent is screened for efficacy in treating or preventing dementia characterized by memory impairment by comparing the performance of a subject or a group of subjects on any of the item-specific retrieval-speed memory tests of the present invention, prior to administration of the candidate agent, with the performance of the subject or the group of subjects on the same memory test, following administration of the candidate agent to the subject or the group of subjects. In the alternative, it is within the confines of the present invention to compare the results of item-specific retrieval-speed memory tests performed by control groups not receiving the candidate agent, with the results of item-specific retrieval-speed memory tests performed by test groups receiving the candidate agent.

By way of example, the method of the present invention may comprise the steps of: (a) assessing semantic memory by one of the methods disclosed herein, so as to obtain a first score; (b) providing a candidate agent to a subject; (c) performing the selected method of step (a) on the subject to obtain a second score; and (d) analyzing the effect of the candidate agent on the second score by comparing the first score to the second score. Semantic memory may be assessed, in order to obtain a first score, by presenting to a subject a cue for retrieving at least one item from semantic memory; having the subject retrieve at least one item from semantic memory; determining (and, optionally, recording) the subject's retrieval speed for each of the items retrieved from semantic memory by the subject; and analyzing the retrieval speeds for the retrieved items in order to assess semantic memory and determine memory impairment. Alternatively, semantic memory may be assessed, in order to obtain a first score, by presenting to a subject a cue for retrieving at least one item from semantic memory; having the subject retrieve at least one item from semantic memory; determining (and, optionally, recording) the subject's retrieval speed for each of the items retrieved from semantic memory by the subject; assigning (and, optionally, recording) a separate weighted value to each of the retrieved items, wherein the value for each retrieved item is weighted according to the speed with which the item is retrieved by the subject; and analyzing the assigned values of the retrieved items in order to assess semantic memory and determine memory impairment.

The present invention also provides a method for measuring semantic memory in a subject. The subject is preferably a mammal (e.g., an ape, a human, a lemur, a monkey, and other primates), and is most preferably a human. The method of the present invention comprises the following: presenting to a subject a cue for retrieving at least one item from semantic memory; having the subject retrieve at least one item from semantic memory; determining (and, optionally, recording) the subject's retrieval speed for each of the items retrieved from semantic memory by the subject; and counting the number of retrieved items for which the retrieval speed is equal to, or less than, a reference speed. In one embodiment of the present invention, the reference speed is the speed at which occurs the greatest difference between the number of items retrieved by control subjects and the number of items retrieved by aged-with-dementia subjects. As disclosed herein, this reference speed may be determined by plotting a graph, for both control subjects and aged-with-dementia subjects, of the number of retrieved items versus time for retrieval, and then ascertaining the speed at which the number of items retrieved by the two populations differs to the greatest extent. Based upon data disclosed herein, an appropriate reference speed may be 1000 msec.

In accordance with the method of the present invention, various methods may be used to determine a subject's retrieval speed for each of the items retrieved from semantic memory by the subject. For example, a fluency test may be administered to determine a subject's retrieval speed for each retrieved item. Examples of such fluency tests include, without limitation, measuring the subject's item-specific speed of antonym recall and measuring the subject's item-specific speed of retrieval in a category-fluency test.

It is understood that, in all of the methods of the present invention described herein, assigned values may be analyzed by calculating a score for the subject based on the retrieval speeds of recalled items, and then comparing the calculated score to a reference score. The reference score may establish memory impairment or may be indicative of a dementia characterized by memory impairment, including, but not limited to, dementia associated with Alzheimer's disease. Additionally, items may be weighted according to any convenient, useful, or desirable parameter, including, but not limited to, retention weighting (presentation weighting, recall weighting, and total-retention weighting), recall state, normative weighting, amplification weighting, retrieval weighting, retrieval-speed weighting, and weighting based upon serial-position effects. Furthermore, the memory-assessment methods of the present invention may be used in conjunction with any form of serial-processing memory test. Finally, item-specific retrieval speeds may be determined within one memory trial, or across two or more memory trials.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Introduction

Measuring the accuracy of retrieval of particular items, by counting the number of items retrieved, is the standard method for measuring memory. Assessing the speed of retrieval, by measuring the time taken to retrieve each of the items, can improve the measurement of memory and the evaluation of memory impairment—both of which are essential to the detection of Alzheimer's disease (AD) and other dementias. A pathologically slow retrieval speed, shown by abnormally long retrieval times, is as significant an indicator of memory impairment as decreased accuracy, shown by retrieval of fewer items.

The measurement of an abnormally slow retrieval speed of a subject who still recalls a normal number of items provides an additional, more subtle, approach to the detection of pre-clinical or very early AD. The identification of individuals who ultimately will progress to clinical AD is important for the selection of subjects for clinical drug trials and for the early treatment that is used to slow or stop progression of the disease. Clinical drug trials are generally designed to show that pharmaceutical treatments can slow the progression of AD and other dementias. In addition, they can demonstrate the benefits of pharmaceutical treatments by showing the treatments' effects on retrieval speed and accuracy.

Item-specific retrieval speed is measured by determining the retrieval time for each item retrieved. Item-specific retrieval speed can be measured most effectively by using cued recall after controlled learning to test the recall of each item. Item-specific retrieval speed also can be measured by paired-associates learning and by free recall.

The discrimination of Alzheimer's disease from other dementias involving memory impairment can be improved by item-specific weighting of recall that gives more credit for faster recall and less credit for slower recall. Slower recall will reduce the memory scores of subjects with memory impairment, and faster recall will increase the memory scores of subjects without memory impairment. As a result, there will be an increase in the difference (effect size) between the memory scores of those with memory impairment and those without memory impairment.

2. Methods a. Measuring Retrieval Speed

Item-specific retrieval speed was determined by measuring the speed of cued recall after controlled learning. After subjects learned a list of 16 items by controlled learning, memory and learning were tested by two trials of encoding-specific cued recall.

(i) Controlled Learning

Controlled learning was carried out by presenting an array of two or more (typically four) items (usually words or pictures) at a time, and asking the subject to identify each of the items when given its category cue. (E.g., "What is the animal?" "Elephant." "What is the Vegetable?" "Carrot.") This procedure was repeated until all of the to-be-remembered items were processed in this manner. The same category cues were then used to elicit cued recall of each item.

Controlled learning, as described above, coordinates acquisition and retrieval. This coordination is necessary in order to elicit effective cued recall. Coordinated acquisition and retrieval optimize encoding specificity, and maximize cued recall for more accurate detection of memory impairment. Controlled learning at acquisition also ensures attention; shows that the subject can identify each item by its category cue; ensures equal processing of all items by specific encoding operations that determine the items that are stored in memory and the retrieval cues that are effective in providing access to the items that are stored (4); induces all subjects to process all items in the same manner on all tests; and shows that the intended processing occurred.

(ii) Cued Recall

Figure 1:
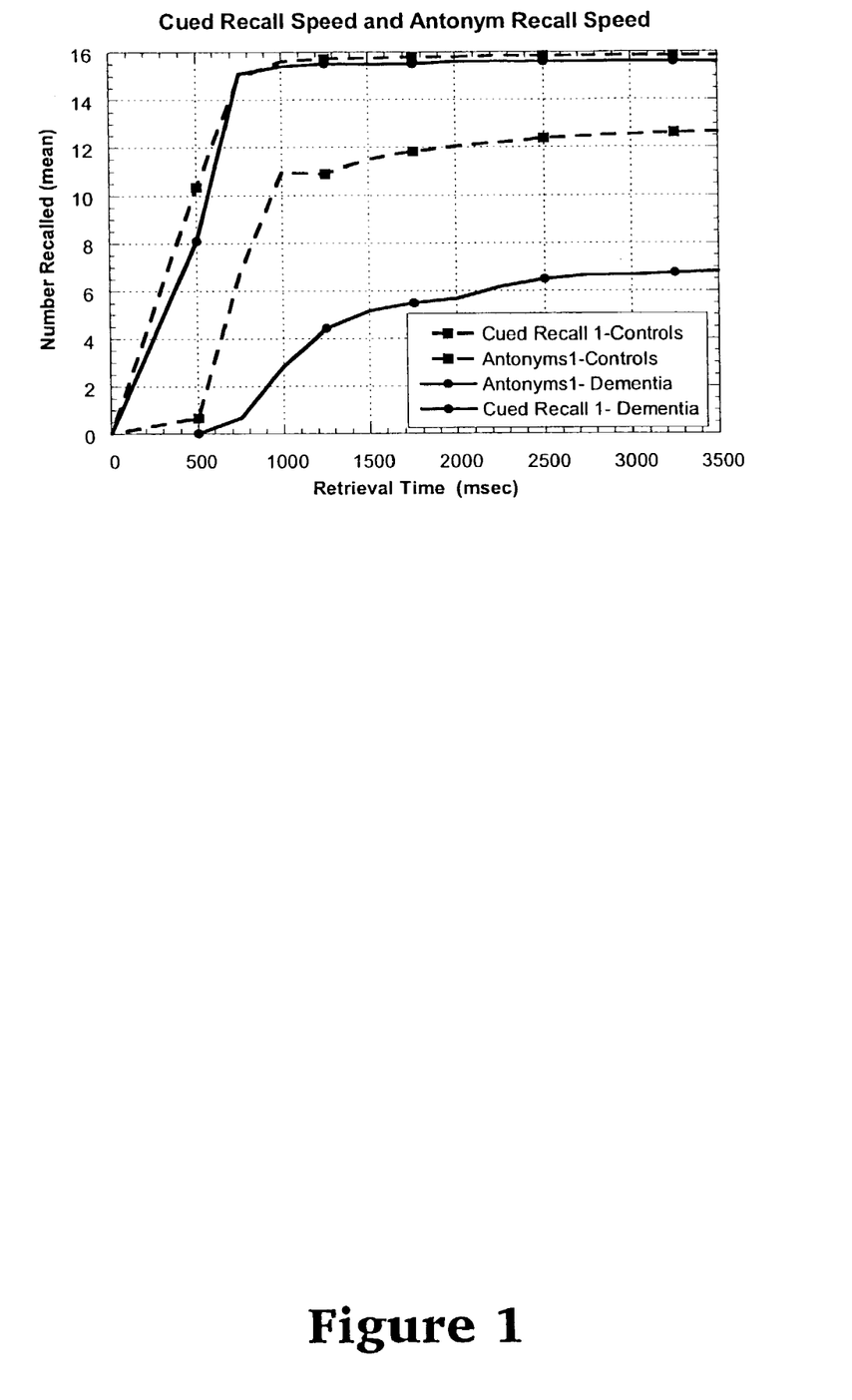
FIG. 1 depicts a speed/accuracy graph that compares cued recall and antonym recall by 146 aged subjects without dementia ("controls") and 9 aged subjects with dementia ("dementia"). The cued recall data show that the aged-with-dementia subjects recalled fewer items more slowly. The antonym recall data (a measure of maximum recall speed) show that aged-with-dementia subjects could recall nearly as quickly as the aged-without-dementia subjects, indicating that slower cued recall by aged-with-dementia subjects was due to their memory impairment, not to generalized or peripheral slowing.

Following controlled learning of all 16 items presented to each subject, cued recall of each item was tested individually, to elicit retrieval of each of the 16 items previously studied in the controlled learning at acquisition. Retrieval time for cued recall was measured from the onset of each cue to the onset of recall (FIG. 1). Such "cued recall after controlled learning" has been shown to increase recall, and to differentially increase the recall by aged-without-dementia subjects over that by aged subjects with Alzheimer's disease, thereby increasing the effect size and improving discrimination (5). Controlled learning, which induces encoding specificity, maximizes recall and should also maximize speed of recall.

When repeated trials were used to measure learning, selective reminding (6) was used before the subsequent trial to remind the subject of any items that were not retrieved on the current trial.

(iii) Item-Specific Retrieval Speed

For each category cue presented, the item-specific speed for retrieving each item was measured from the onset of the category cue to the onset of the response item elicited by that category cue. This provided a measure of retrieval time for each item, based on actual retrieval of each item. Item-specific retrieval times can be used for item-specific weighting of recall, in order to improve the measurement of memory and the detection of memory impairment and Alzheimer's disease.

(iv) Maximum Retrieval Speed

In order to obtain a measurement of each subject's fastest retrieval speed for rapidly-retrievable memory ("maximum retrieval speed"), familiar words were presented to the subject for the purpose of eliciting their opposites. Each subject was asked to recall the antonym (opposite) of a very well-known, and frequently-used, simple item that has a specific, very well-known, frequently-used, and easily-retrieved antonym (opposite). (E.g., present "in", recall "out"; present "up", recall "down"; present "yes", recall "no".) Maximum retrieval speed was measured from the onset of each cue to the onset of antonym retrieval (FIG. 1).

A measurement of maximum recall speed provides a baseline measure of retrieval, and can be used to demonstrate that slower cued recall is due to memory impairment, and not to generalized slowing of cognitive processing or non-specific peripheral slowing (e.g., slower speech). Antonym recall speed provides one measurement of maximum recall speed. Maximum antonym retrieval speed appears to be less affected by aging, memory impairment, and dementia; thus, it may serve as a "hold" measure with which current retrieval speeds for memory and learning can be compared in order to obtain an estimate of change in memory performance.

(v) Delayed Cued Recall

Reading times for the items to-be-remembered and for the category cues were also measured. To measure forgetting, delayed cued recall was measured after a delay following the initial testing of cued recall. A second trial also was added to measure savings by faster retrieval speed on the second trial.

(vi) Sequence of Tests for Measuring Retrieval Speed

To measure retrieval speed, firstly, item reading time was measured for each of the list items as they were read aloud by the subject. Secondly, controlled learning of the items was carried out. Thirdly, cued recall of all items was elicited in two trials. To measure learning by faster retrieval speed on the second trial, selective reminding was used before the second trial. Fourthly, category cue reading time was measured for each of the category cues as it was read aloud by the subject.

Subsequently, controlled learning of antonyms was performed by giving the subject the antonym for each of the antonym cues (without speed measurement). This is sufficient for controlled learning when there is only one response to each cue. Cued recall of all antonyms then was measured in two trials, in order to measure implicit memory (priming) on the second trial. Finally, delayed cued recall was tested in two trials. The second trial was used to measure savings, shown by faster retrieval speed on the second trial.

The above-described sequence of tests provides one method that was used for measuring retrieval speeds. All steps of the sequence need not be performed, and any individual step may be performed alone. For example, cued recall alone could be tested.

b. Statistical Analyses 313 subjects were given the Cued Recall Test. At the time of testing, 20 subjects had dementia, and 293 did not. The total number of items recalled on the first recall trial were calculated for each subject ("CUE"=cued recall). In addition, the 90% trimmed mean of the reaction time among the correct cued recall items was calculated for each subject ("MRT"=mean reaction time).

The Receiver Operating Characteristic (ROC) functions were obtained through logistic regression. The Cued Recall Test models were compared. In Model 1, only mean reaction time (MRT) was included as a predictor; in Model 2, only the number of items correctly recalled (CUE) was used as a predictor. In Model 3, both MRT and CUE were included as predictors.

Each unique predicted probability for the subjects may be used as a possible cut for diagnosis of dementia. Accordingly, sensitivity and specificity were calculated for each such cut for each of the three models. Thus, three ROC functions were computed. For a common level of sensitivity, the specificities obtained for the three models were compared using McNemar's test. Where the specificity for Model 3 is significantly higher than that for Models 1 and 2, it signifies that mean reaction time together with total recall better discriminate between persons with dementia and those without than does either measure alone.

3. Results a. Measuring Retrieval Speed

Tables 1 and 2 show retrieval times in the cued recall of items and antonyms, by the following test subjects: a normal young adult; an aged adult without dementia; an aged adult with dementia; and an aged adult with possible, very early or "pre-clinical" dementia. Recall is indicated in Tables 1 and 2 by retrieval time for each item recalled; cells without recall times indicate recall failure. Statistics for timed cued recall, for dementia and mild cognitive impairment (MCI) groups, are presented in Table 3. As these examples show, retrieval speed is slower in subjects with dementia, with relative preservation of maximum (antonym) retrieval speed.

FIG. 1 shows the number of items recalled, as the time for recall increases. The asymptotes show the total number of items recalled by 3500 msec, as a measurement of capacity. The rate at which recall increases to reach the asymptote reflects retrieval speed; where recall more slowly increases to reach the asymptote, more time is needed for retrieval.

According to the data presented in FIG. 1, the aged-with-dementia subjects did not merely have lower cued recall, as shown by their lower asymptote; rather, they also recalled more slowly, as shown by the slower rate at which their cued recall increased to reach their asymptote. Cued recall by the aged-with-dementia subjects required much longer retrieval times to reach the asymptote than did cued recall by the aged-without-dementia subjects. Nearly all of the items recalled by the aged-without-dementia (control) subjects were recalled in less than 1000 msec, but recall of most items by the aged-with-dementia subjects required more than 1000 msec. Since the difference between cued recall by control subjects and cued recall by the aged-with-dementia subjects is greatest at 1000 msec, detection of memory impairment may be improved by counting the number of items that are recalled within 1000 msec.

TABLE 1

Memory Assessment by Measurement of Retrieval Speed
Memory Assessment by Retrieval Speed

| | | | | Item Cued Recall | | | | Antonym Recall | | | | Delayed Recall | | Weighted Recall* |
| | | | Read | Trial 1 | | Trial 2 | | Read | Trial 1 | | Trial 2 | | | | |
| Status | Age | ID | Items | # | RT | # | RT | Cues | # | RT | # | RT | # | RT | (Trial 1) |
|---|---|---|---|---|---|---|---|---|---|---|---|---|---|---|---|
| Young | 28 | KZ4444 | 604 | 16 | 604 | 16 | 535 | 287 | 16 | 443 | 16 | 411 | 16 | 535 | 26.5 |
| Aged | 86 | EK8042 | 310 | 15 | 634 | 15 | 541 | 313 | 16 | 367 | 16 | 354 | 15 | 617 | 25.2 |
| Dementia | 74 | LJ9055 | 384 | 11 | 2781 | 13 | 2085 | 307 | 16 | 505 | 16 | 525 | 9 | 1348 | 3.9 |
| Pre-clinical | 80 | UM8573 | 540 | 11 | 1542 | 9 | 1043 | 538 | 16 | 782 | 16 | 999 | 13 | 1480 | 7.1 |

RT = retrieval time
weighted recall = (# recalled retrieval time) × 1000

TABLE 2

Cued Recall and Antonym Recall

Normal Young Adult / KZ4444 28-year-old normal woman

| | read items | Item C.L. | Item recall 1 | Item recall 2 | change | read cues | Ant C.L. | Antonym recall 1 | Antonym recall 2 | Delayed Item recall |
|---|---|---|---|---|---|---|---|---|---|---|
| 1 | 389 | + | 853 | 596 | − | 356 | + | 424 | 391 | 544 |
| 2 | 400 | + | 692 | 646 | − | 278 | + | 366 | 521 | 542 |
| 3 | 356 | + | 539 | 474 | − | 278 | + | 395 | 328 | 513 |
| 4 | 361 | + | 952 | 670 | − | 239 | + | 433 | 391 | 603 |
| 5 | 360 | + | 555 | 480 | − | 270 | + | 373 | 361 | 469 |
| 6 | 368 | + | 486 | 490 | + | 262 | + | 473 | 388 | 503 |
| 7 | 373 | + | 481 | 478 | − | 271 | + | 399 | 465 | 487 |
| 8 | 392 | + | 607 | 523 | − | 308 | + | 357 | 402 | 510 |
| 9 | 361 | + | 559 | 546 | − | 314 | + | 393 | 433 | 561 |
| 10 | 397 | + | 487 | 477 | − | 335 | + | 411 | 382 | 516 |
| 11 | 342 | + | 544 | 447 | − | 319 | + | 443 | 390 | 503 |
| 12 | 378 | + | 672 | 547 | − | 288 | + | 522 | 441 | 585 |
| 13 | 409 | + | 627 | 516 | − | 275 | + | 623 | 473 | 537 |
| 14 | 390 | + | 626 | 574 | − | 333 | + | 466 | 369 | 680 |
| 15 | 391 | + | 531 | 483 | − | 245 | + | 425 | 389 | 557 |
| 16 | 288 | + | 451 | 613 | + | 222 | + | 584 | 460 | 453 |
| Mean | 372 | | 604 | 535 | | 287 | | 443 | 411 | 535 |

Normal Aged Adult / EK8042 86-year-old woman without dementia

| | read items | Item C.L. | Item recall 1 | Item recall 2 | change | read cues | Ant C.L. | Antonym recall 1 | Antonym recall 2 | Delayed Item recall |
|---|---|---|---|---|---|---|---|---|---|---|
| 1 | 382 | + | 1067 | 405 | − | 539 | + | 364 | 299 | 2088 |
| 2 | 360 | + | 541 | 467 | − | 269 | 0 | 355 | 462 | 559 |
| 3 | 293 | + | 457 | 429 | − | 311 | + | 342 | 318 | 382 |
| 4 | 273 | + | 617 | 1103 | + | 271 | + | 363 | 317 | 572 |
| 5 | 266 | + | 400 | 519 | + | 330 | 0 | 361 | 303 | 398 |
| 6 | 302 | + | 362 | 367 | + | 277 | + | 506 | 314 | 483 |
| 7 | 308 | + | 544 | 431 | − | 287 | + | 427 | 327 | 424 |
| 8 | 276 | + | 622 | 448 | − | 286 | + | 358 | 300 | 447 |
| 9 | 273 | + | 429 | 369 | − | 283 | + | 353 | 303 | 393 |
| 10 | 283 | + | 983 | 1261 | + | 323 | + | 403 | 336 | 752 |
| 11 | 280 | + | 678 | 407 | − | 281 | + | 349 | 342 | 492 |
| 12 | 333 | + | 482 | 396 | − | 296 | + | 334 | 327 | 491 |
| 13 | 391 | + | 520 | 580 | + | 348 | + | 344 | 336 | 439 |
| 14 | 288 | + | 1133 | 406 | − | 297 | + | 309 | 293 | 459 |
| 15 | 315 | + | | | | 288 | + | 366 | 264 | |
| 16 | 345 | + | 678 | 531 | − | 330 | + | 336 | 983 | 875 |
| Mean | 310 | | 634 | 541 | | 313 | | 367 | 364 | 617 |

TABLE 2-continued

Cued Recall and Antonym Recall

| | Dementia | | | | | LJ8501 79-year-old woman with dementia | | | | | |
|---|---|---|---|---|---|---|---|---|---|---|---|
| | read items | Item C.L. | Item recall 1 | Item recall 2 | change | read cues | Ant C.L. | Antonym recall 1 | Antonym recall 2 | Delayed Item recall |
| 1 | 335 | + | | 2361 | | 327 | + | 412 | 379 | 2487 |
| 2 | 393 | + | 780 | 645 | − | 277 | + | 439 | 411 | 705 |
| 3 | 337 | + | | | | 275 | + | 399 | 314 | |
| 4 | 314 | + | 4041 | 1389 | − | 265 | + | 589 | 501 | |
| 5 | 413 | + | 773 | 703 | − | 378 | + | 494 | 640 | 726 |
| 6 | 327 | + | 1284 | 671 | − | 283 | + | 485 | 403 | 2231 |
| 7 | 390 | + | 3317 | 2623 | − | 302 | + | 486 | 469 | |
| 8 | 339 | + | | | | 281 | + | 372 | 395 | |
| 9 | 362 | + | 1326 | 1259 | − | 288 | + | 775 | 843 | 1811 |
| 10 | 343 | + | | | | 307 | + | 474 | 454 | |
| 11 | 329 | + | | 7424 | | 349 | + | 524 | 461 | |
| 12 | 358 | + | 980 | 1250 | + | 272 | + | 809 | 921 | 1075 |
| 13 | 372 | + | 3058 | 1483 | − | 346 | + | 449 | 478 | 1142 |
| 14 | 635 | + | 6863 | 3590 | − | 307 | + | 418 | 419 | |
| 15 | 495 | + | 7350 | 3077 | − | 299 | + | 444 | 752 | 905 |
| ** | 397 | + | 818 | 636 | − | 348 | + | 515 | 553 | 1052 |
| Mean | 384 | | 2781 | 2085 | | 307 | | 505 | 525 | 1348 |

| | ? Pre-Clinical Dementia ? | | | | | UM8573 80-year-old woman with ? pre-clinical dementia ? | | | | | |
|---|---|---|---|---|---|---|---|---|---|---|---|
| | read items | C.L. items | 1st recall (11) | 2nd recall (9) | change | read cues | Ant C.L. | Antonym recall 1 | Antonym recall 2 | Delayed recall (13) |
| 1 | 677 | + | 4104 | 1153 | − | 864 | + | 539 | 655 | |
| 2 | 541 | + | 2501 | | | 582 | + | 524 | 432 | 3875 |
| 3 | 729 | + | 1172 | 1551 | + | 460 | + | 485 | 483 | 2619 |
| 4 | 496 | + | | | | 444 | + | 569 | 4366 | 3801 |
| 5 | 553 | + | 1022 | 877 | − | 431 | + | 497 | 546 | 649 |
| 6 | 541 | + | 1187 | 832 | − | 536 | + | 1248 | 1790 | 727 |
| 7 | 480 | + | 744 | 1150 | + | 430 | + | 627 | 545 | 728 |
| 8 | 471 | + | 1623 | | | 487 | + | 698 | 477 | 712 |
| 9 | 513 | + | | 1555 | | 698 | + | 521 | 787 | 697 |
| 10 | 523 | + | 1402 | 743 | − | 809 | + | 1070 | 1315 | 1017 |
| 11 | 538 | + | 1021 | 795 | − | 516 | + | 694 | 781 | 774 |
| 12 | 476 | + | 723 | 734 | + | 445 | + | 491 | 458 | 1360 |
| 13 | 523 | + | | | | 432 | + | 867 | 597 | 1307 |
| 14 | 526 | + | | | | 435 | + | 545 | 502 | |
| 15 | 526 | + | 1465 | | | 424 | + | 739 | 1298 | 971 |
| 16 | 526 | + | | | | 619 | + | 2393 | 953 | |
| Mean | 540 | | 1542 | 1043 | | 538 | | 782 | 999 | 1480 |

C.L. = controlled learning
Ant = antonym

TABLE 3

Statistics for the Timed Cued Recall: Dementia and MCI

| | Control Group (includes MCI) | Dementia | Sig-nificance | Non-MCI Control Group | MCI* | Sig-nificance |
|---|---|---|---|---|---|---|
| N | 293 | 21 | | 235 | 58 | |
| Age | 78.1 (5.3) | 80.6 (.4) | NS | 78.1 (5.3) | 79.3 (5.9) | NS |
| Education | 13.1 (3.4) | 11.8 (3.7) | NS | 13.1 (3.4) | 13.4 (3.7) | NS |
| Sex (% male) | 30 | 20 | NS | 42 | 57 | NS |
| Ethnic (% caucasian) | 70 | 72 | NS | 70 | 80 | NS |
| SumTot3 | 47.8 (1.2) | 27.5 (8.5) | .000 | 47.9 (0.4) | 46.8 (2.4) | .001 |
| BIMC | 2.6 (2.4) | 8.7 (3.8) | .000 | 2.3 (2.2) | 3.8 (3.0) | .000 |
| GDS | 2.7 (2.4) | 5.5 (3.6) | .002 | 2.5 (2.3) | 3.3 (2.5) | .028 |
| WRAT reading | 68.7 (15.5) | 65.2 (14.1) | NS | 69.0 (15.3) | 67.6 (16.4) | NS |

TABLE 3-continued

Statistics for the Timed Cued Recall: Dementia and MCI

|  | Control Group (includes MCI) | Dementia | Sig-nificance | Non-MCI Control Group | MCI* | Sig-nificance |
|---|---|---|---|---|---|---|
| Cued Recall | 13.2 (2.4) | 8.2 (3.4) | .000 | 13.6 (2.2) | 11.8 (2.8) | .000 |
| Mean RT (correct) | 964 (356) | 1340 (481) | .002 | 939 (323) | 1065 (457) | .051 |

SumTot3 = the sum of total recall over the three trials
BIMC = Blessed Information-Memory-Concentratioin
GDS = Geriatric Depression Scale
WRAT = Wide-Range Achievement Test
RT = retrieval time
MCI defined by robust norms on SumFree3 (the sum of free recall over the three trials) (<25).

b. Statistical Analyses

Table 4 shows the mean and standard deviation of cued recall (CUE) and mean reaction time (MRT) for dementia (case) and non-dementia (control) subjects. Table 5 provides the median and the 95% non-parametric confidence limits of cued recall and mean reaction time for dementia and non-dementia subjects. Using a Mann-Whitney (or Wilcoxon Rank Sum) test, the inventor has shown in Table 6 that the locations of the distributions of case and control of both cued recall and mean reaction time differ significantly.

TABLE 4

|  | Case | | Non-Case | |
|---|---|---|---|---|
|  | Mean | SD | Mean | SD |
| cued recall | 8.25 | 2.9357147 | 13.221843 | 2.4358764 |
| reaction time | 1380.78 | 587.5082946 | 873.7089526 | 310.1971483 |

TABLE 5

|  | Case | | Non-Case | |
|---|---|---|---|---|
|  | Median | 95% CI | Median | 95% CI |
| cued recall | 8 | 6-10 | 14 | 13-14 |
| mean reaction time | 1228.438 | 1039.286-1562.5 | 790.7692 | 761.3-821.6667 |

CI = confidence interval

TABLE 6

|  | Mann-Whitney Test | |
|---|---|---|
|  | Approx [Z] | p-value |
| cued recall | 6.0317 | <.0001 |
| mean reaction time | 5.1445 | <.0001 |

The ROC curves for Models 1, 2, and 3 (data not shown) revealed that the use of both cued recall and reaction time produced higher specificity than did the use of reaction time alone, for sensitivities between 0.35 and 0.95. In addition, use of both cued recall and reaction time produced higher specificities for sensitivities between 0.60 and 0.95. Table 7 shows this quantitatively, for two sensitivities of potential interest.

Table 8 provides the odds ratio of specificity between any two of the three models when sensitivity is at 0.8 or 0.9. We also perform a McNemar's test under the null hypothesis of equal specificity vs. the alternative hypothesis of different specificity between any two of the three models. The p-values suggest that the differences in Table 5 are all significant when sensitivity is fixed at 0.8 or 0.9.

TABLE 7

| specificity | sensitivity = 0.8 | sensitivity = 0.9 |
|---|---|---|
| reaction time only (Model 1) | 0.7884 | 0.6553 |
| recall only (Model 2) | 0.8771 | 0.7816 |
| recall + reaction time (Model 3) | 0.9078 | 0.8191 |

TABLE 8

|  | sensitivity = 0.8 | | sensitivity = 0.9 | |
|---|---|---|---|---|
|  | odds ratio | p-value | odds ratio | p-value |
| Model 2 vs. Model 1 | 1.9154 | 0.0006 | 1.8825 | <.0001 |
| Model 3 vs. Model 1 | 2.6426 | <.0001 | 2.3818 | <.0001 |
| Model 3 vs. Model 2 | 1.3796 | 0.0126 | 1.2652 | 0.0076 |

4. Discussion

The inventor has described herein an effective method for measuring item-specific retrieval speed by determining the speed of cued recall after controlled learning. This method provides data concerning both item-specific recall and item-specific retrieval speed that is needed to measure memory and learning more completely, accurately, and effectively.

Measurement of item-specific retrieval times indicates that memory impairment in dementia may be associated with slower retrieval speed. Therefore, the measurement of memory, the detection of memory impairment, and the detection of Alzheimer's disease and other dementias of which memory impairment is an early indication, can be improved by memory testing that includes item-specific retrieval times in addition to the number of items retrieved.

Item-specific retrieval speed can be used in several ways to improve memory measurement and detection of memory impairment. For example, retrieval speed can be used by itself to measure memory and to detect memory impairment, in the same manner as accuracy (number of items correctly retrieved) is currently used to measure memory and to detect memory impairment. Additionally, retrieval speed can be used for item-specific weighting, in order to obtain memory scores that reflect both the number of items retrieved (accuracy) and the speed of retrieval. When retrieval is weighted by retrieval time, items retrieved rapidly (shorter retrieval time) receive more credit than items retrieved slowly (longer retrieval time).

Retrieval speed also can be regressed on accuracy to identify abnormally slow retrieval speed, given the number of items retrieved. Furthermore, retrieval speed can be used as a covariant in analyses of memory. In addition, retrieval speed can be used to measure learning over repeated trials, wherein learning is shown by a decrease in retrieval time (as well as by an increase in number of items retrieved). Finally, retrieval speed can be used to measure a change in memory and cognition, in the same manner as accuracy (number of items retrieved) is currently used.

Slowing of retrieval speed may occur before a decrease in the number of items recalled, i.e., when the number of items recalled is still within the normal range. Therefore, this new, more subtle method for measuring memory and detecting memory impairment by retrieval speed should be useful for the detection of very early or "pre-clinical" Alzheimer's disease and other dementias, even when the number of items recalled is still within the normal range. Additionally, this method for measuring both retrieval speed and recall also should be useful for assessing treatment effects of pharmaceuticals in drug trials.

Finally, based upon statistical analyses disclosed herein, it appears that use of reaction time along with cued recall results in higher specificity for prevalent dementia than does the use of either measurement alone.

REFERENCES

1. Callahan et al., Documentation and evaluation of cognitive impairment in elderly primary care patients. *Ann. Intern. Med.*, 122(6):422-29, Mar. 15, 1995.
2. White and Davis, *J. Gen. Intern. Med.*, 5:438-45, 1990.
3. Beers and Berkow (eds.), *The Merck Manual of Diagnosis and Therapy*, 17th ed. (Whitehouse Station, N.J.: Merck Research Laboratories, 1999) 1393.
4. Tulving and Thomson, *Psychological Review*, 80:352-72, 1973.
5. Buschke et al., *Neurology*, 48(4):989-97, April 1997.
6. Buschke, H., *Journal of Verbal Learning and Verbal Behavior*, 12:543-50, 1973.
7. Tulving, E., *Can. Psychol.*, 26:1-12, 1985.
8. Gardiner et al., *Can. J. Exp. Psychol.*, 50:114-122, 1996.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for assessing memory in a subject, comprising the steps of:
    (a) presenting to a subject a list of items to be retrieved from memory by the subject, wherein the items are presented to the subject using controlled learning where the subject identifies the items from a cue associated with the item before proceeding to step (b);
    (b) having the subject retrieve the presented items from memory, wherein the items are retrieved using cued recall where the subject recalls the items following presentation of the cue previously associated with the item;
    (c) determining the subject's retrieval speed for each of the items retrieved from memory by the subject; and
    (d) analyzing the retrieval speeds for the retrieved items, wherein retrieval speed is the continuous time period that is required between the time when the subject is asked to retrieve an item from memory and the time when the subject retrieves the item from memory, and wherein the step of determining the subject's retrieval speed comprises measuring the subject's item-specific speed of cued recall after controlled learning.

2. The method of claim 1, wherein the step of determining the subject's retrieval speed comprises measuring the subject's item-specific speed of paired-associates learning.

3. The method of claim 1, wherein the step of determining the subject's retrieval speed comprises measuring the subject's item-specific speed of free recall.

4. The method of claim 1, wherein the step of analyzing the retrieval speeds comprises calculating a memory score for the subject based on the retrieval speeds, and comparing the memory score to a reference score.

5. The method of claim 4, wherein the reference score establishes memory impairment.

6. The method of claim 5, wherein the memory impairment is indicative of dementia.

7. The method of claim 6, wherein the dementia is associated with Alzheimer's disease.

8. The method of claim 5, wherein the memory impairment is indicative of pre-clinical Alzheimer's disease, early Alzheimer's disease, mild cognitive impairment (MCI), age-related cognitive decline, mild neurocognitive disorder, or delirium.

9. A method for screening for an agent directed to treating, slowing down the progress of, attenuating the symptoms of, or preventing dementia characterized by memory impairment, comprising the steps of:
    (a) performing the method of claim 1 to obtain a first score;
    (b) providing a candidate agent to a subject;
    (c) performing the selected method of step (a) on the subject to obtain a second score; and
    (d) analyzing the effect of the candidate agent on the second score by comparing the first score to the second score.

10. The method of claim 1, wherein the step of determining the subject's retrieval speed comprises measuring the subject's item-specific speed of antonym recall.

11. The method of claim 10, wherein the subject's speed of antonym recall provides a measure of the subject's maximum recall speed with which the subject's retrieval speed is compared to obtain an estimate of change in memory performance.

12. The method of claim 10, wherein the subject's speed of antonym recall provides a measure of the subject's maximum recall speed with which the subject's retrieval speed is compared to obtain an estimate of memory performance that is adjusted for generalized slowing of cognitive processing and non-specific peripheral slowing.

13. The method of claim 1, wherein the memory is episodic memory.

14. The method of claim 1, wherein the memory is semantic memory.

15. A method for assessing memory in a subject, comprising the steps of:
    (a) presenting to a subject a list of items to be retrieved from memory by the subject, wherein the items are presented to the subject using controlled learning where the subject identifies the items from a cue associated with the item before proceeding to step (b);
    (b) having the subject retrieve the presented items from memory, wherein the items are retrieved using cued recall where the subject recalls the items following presentation of the cue previously associated with the item;

(c) determining the subject's retrieval speed for each of the items retrieved from memory by the subject;

(d) assigning a separate weighted value to each of the retrieved items, wherein the value for each retrieved item is weighted according to the speed with which the item is retrieved by the subject; and (e) analyzing the assigned values of the retrieved items, wherein retrieval speed is the continuous time period that is required between the time when the subject is asked to retrieve an item from memory and the time when the subject retrieves the item from memory, and wherein the step of determining the subject's retrieval speed comprises measuring the subject's item-specific speed of cued recall after controlled learning.

16. The method of claim 15, further comprising introducing a delay between the steps of presenting to the subject the list of items and having the subject retrieve the presented items.

17. The method of claim 16, wherein the delay is an interference delay.

18. The method of claim 15, wherein the step of determining the subject's retrieval speed comprises measuring the subject's item-specific speed of paired-associates learning.

19. The method of claim 15, wherein the step of determining the subject's retrieval speed comprises measuring the subject's item-specific speed of free recall.

20. The method of claim 15, wherein the assigned values are further weighted according to the number of items retrieved by the subject.

21. The method of claim 15, wherein the assigned values are further weighted according to the order in which the items are renieved by the subject.

22. The method of claim 15, wherein the assigned values are further weighted according to the relative difficulty of retrieving each item.

23. The method of claim 15, wherein the assigned values are further weighted according to the speed with which each item is retrieved by members of a reference group.

24. The method of claim 15, wherein the step of analyzing the assigned values comprises calculating a memory score for the subject based on the weighted values, and comparing the memory score to a reference score.

25. The method of claim 24, wherein the reference score establishes memory impairment.

26. The method of claim 25, wherein the memory impairment is indicative of dementia.

27. The method of claim 26, wherein the dementia is associated with Alzheimer's disease.

28. The method of claim 25, wherein the memory impairment is indicative of pre-clinical Alzheimer's disease, early Alzheimer's disease, mild cognitive impairment (MCI), age-related cognitive decline, mild neurocognitive disorder, or delirium.

29. The method of claim 15, wherein the step of determining the subject's retrieval speed comprises measuring the subject's item-specific speed of antonym recall.

30. The method of claim 29, wherein the subject's speed of antonym recall provides a measure of the subject's maximum recall speed with which the subject's retrieval speed is compared to obtain an estimate of change in memory performance.

31. The method of claim 29, wherein the subject's speed of antonym recall provides a measure of the subject's maximum recall speed with which the subject's retrieval speed is compared to obtain an estimate of memory performance that is adjusted for generalized slowing of cognitive processing and non-specific peripheral slowing.

32. The method of claim 15, wherein the memory is episodic memory.

33. The method of claim 15, wherein the memory is semantic memory.

34. A method for screening for an agent directed to treating, slowing down the progress of, attenuating the symptoms of, or preventing dementia characterized by memory impairment, comprising the steps of:

(a) performing the method of claim 15 to obtain a first score;

(b) providing a candidate agent to a subject;

(c) performing the selected method of step (a) on the subject to obtain a second score; and (d) analyzing the effect of the candidate agent on the second score by comparing the first score to the second score.

35. A method for measuring memory in a subject, comprising the steps of:

(a) presenting to a subject a list of items to be retrieved from memory by the subject, wherein the items are presented to the subject using controlled learning where the subject identifies the items from a cue associated with the item before proceeding to step (b);

(b) having the subject retrieve the presented items from memory, wherein the items are retrieved using cued recall where the subject recalls the items following presentation of the cue previously associated with the item;

(c) determining the subject's retrieval speed for each of the items retrieved from memory by the subject; and (d) counting the number of retrieved items for which the retrieval speed is equal to, or less than, a reference speed, wherein retrieval speed is the continuous time period that is required between the time when the subject is asked to retrieve an item from memory and the time when the subject retrieves the item from memory, and wherein the step of determining the subject's retrieval speed comprises measuring the subject's item-specific speed of cued recall after controlled learning.

36. The method of claim 35, wherein the reference speed is the speed at which occurs the greatest difference between the number of items retrieved by control subjects and the number of items retrieved by aged-with-dementia subjects.

37. The method of claim 36, wherein the reference speed is 1000 msec.

38. The method of claim 35, wherein the step of determining the subject's retrieval speed comprises measuring the subject's item-specific speed of paired-associates learning.

39. The method of claim 35, wherein the step of determining the subject's retrieval speed comprises measuring the subject's item-specific speed of free recall.

40. The method of claim 35, wherein the step of determining the subject's retrieval speed comprises measuring the subject's item-specific speed of antonym recall.

41. The method of claim 40, wherein the subject's speed of antonym recall provides a measure of the subject's maximum recall speed with which the subject's retrieval speed is compared to obtain an estimate of change in memory performance.

42. The method of claim 40, wherein the subject's speed of antonym recall provides a measure of the subject's maximum recall speed with which the subject's retrieval speed is compared to obtain an estimate of memory performance that is adjusted for generalized slowing of cognitive processing and non-specific peripheral slowing.

43. The method of claim 35, wherein the memory is episodic memory.

44. The method of claim 35, wherein the memory is semantic memory.

45. A method for screening for an agent directed to treating, slowing down the progress of, attenuating the symptoms of, or preventing dementia characterized by memory impairment, comprising the steps of:

(a) performing the method of claim 35 to obtain a first score;
(b) providing a candidate agent to a subject;
(c) performing the selected method of step (a) on the subject to obtain a second score; and
(d) analyzing the effect of the candidate agent on the second score by comparing the first score to the second score.

* * * * *